United States Patent [19]

Richardson et al.

[11] Patent Number: 4,818,470
[45] Date of Patent: Apr. 4, 1989

[54] APPARATUS FOR THE ULTRASONIC EXAMINATION OF SHROUD HOLD DOWN BOLTS

[75] Inventors: David L. Richardson, Los Gatos; Jack P. Clark, San Jose; Thurman D. Smith, San Jose; Richard W. Perry, San Jose, all of Calif.

[73] Assignee: General Electric Company, San Jose, Calif.

[21] Appl. No.: 91,174

[22] Filed: Aug. 31, 1987

[51] Int. Cl.$^4$ .............................................. G21C 17/00
[52] U.S. Cl. ...................................... 376/245; 73/632
[58] Field of Search ............... 376/245, 249, 252, 260; 73/627, 629, 632

[56] References Cited

U.S. PATENT DOCUMENTS

| 4,350,044 | 9/1982 | Richardson et al. | 73/632 |
| 4,509,369 | 4/1985 | Kuljis et al. | 73/627 |
| 4,689,994 | 9/1987 | Savinell et al. | 376/252 |
| 4,741,878 | 5/1988 | Gebelin et al. | 376/245 |

FOREIGN PATENT DOCUMENTS

| 0213028 | 3/1987 | European Pat. Off. | 376/245 |
| 0039655 | 3/1979 | Japan | 376/245 |
| 0164152 | 7/1986 | Japan | 376/245 |
| 0290357 | 12/1986 | Japan | 73/627 |

*Primary Examiner*—Deborah L. Kyle
*Assistant Examiner*—Daniel Wasil
*Attorney, Agent, or Firm*—Robert R. Schroeder

[57] ABSTRACT

An apparatus for the remote examination of peripheral shroud hold down bolts on steam separators used in boiling water reactors is disclosed. The testing apparatus is used while the steam separator is in a holding pool. The testing apparatus includes a depending pole having attached at the bottom thereof an aluminum shoe. The shoe has a flat, upwardly exposed bottom and opens to one side at gathering surfaces to receive the lower ends of the shroud bolts. The upwardly exposed bottom of the shoe defines an aperture through which an upwardly exposed piezoelectric device is exposed for direct contact with the bottom of the bolt. An overlying clamp member is provided to clamp the lug onto the bottom of the shoe for testing. The clamp member defines a receiving slot to receive the shaft of the bolt immediately overlying the rectangular lug. The clamp member slides over the shaft at the slot into contact with the top of the lug. The clamp member clamps the lug end of the bolt securely onto the upwardly exposed piezoelectric device on the upwardly exposed bottom of the shoe. A piezoelectric ultrasonic test is then run from the bottom and radioactive portion of the bolt to and towards the top of the bolt. Testing for longitudinal sound waves, refracted sound waves and shear sound waves for inter granular stress corrosion cracking can occur despite the radioactive and remote under water location of the bolts.

5 Claims, 5 Drawing Sheets

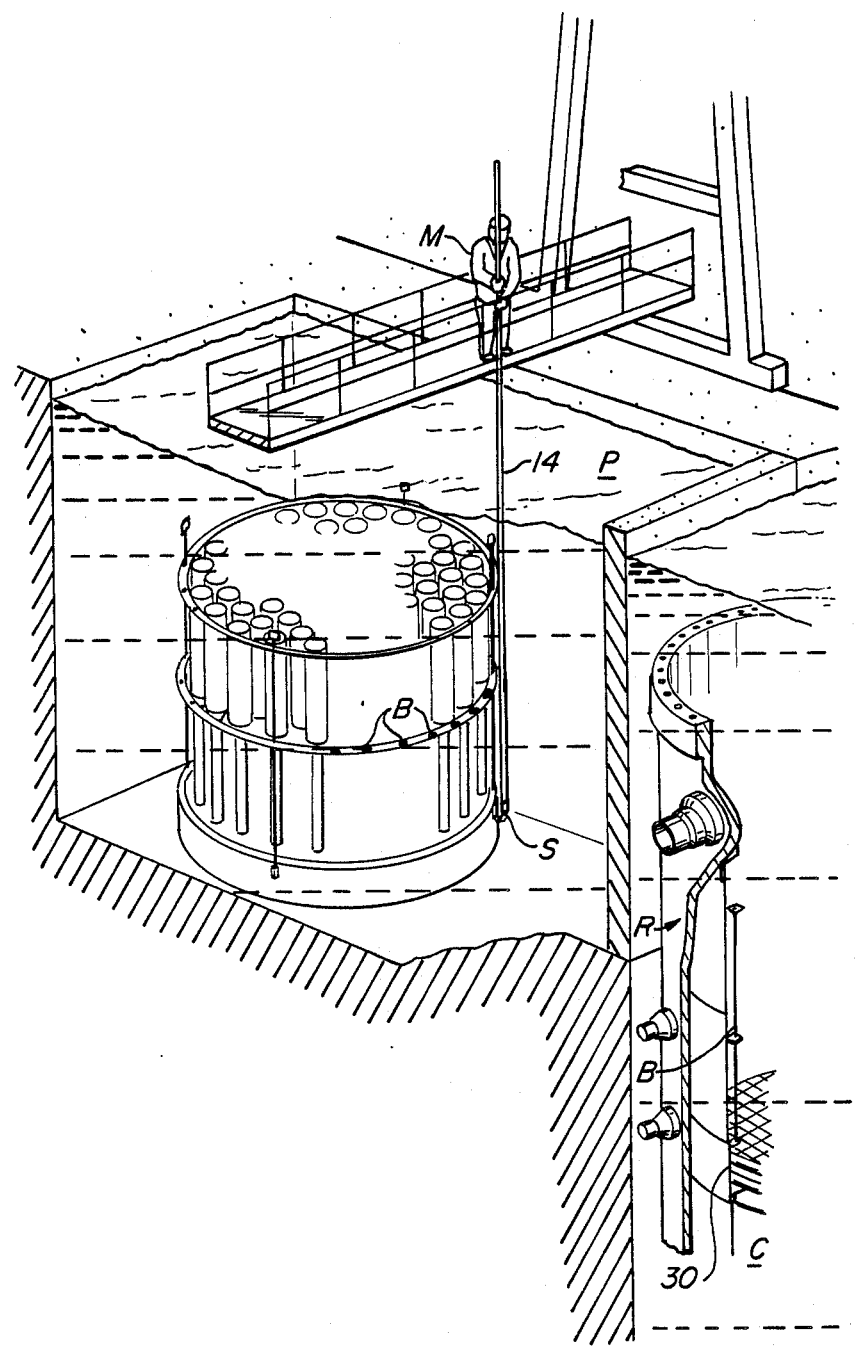
FIG._1.

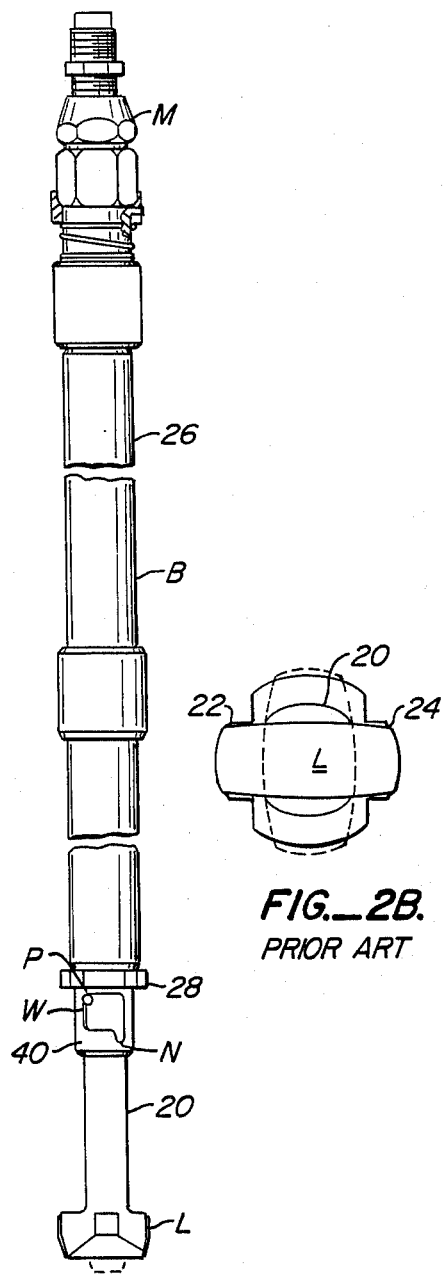
FIG._2B.
PRIOR ART
FIG._2A.
PRIOR ART

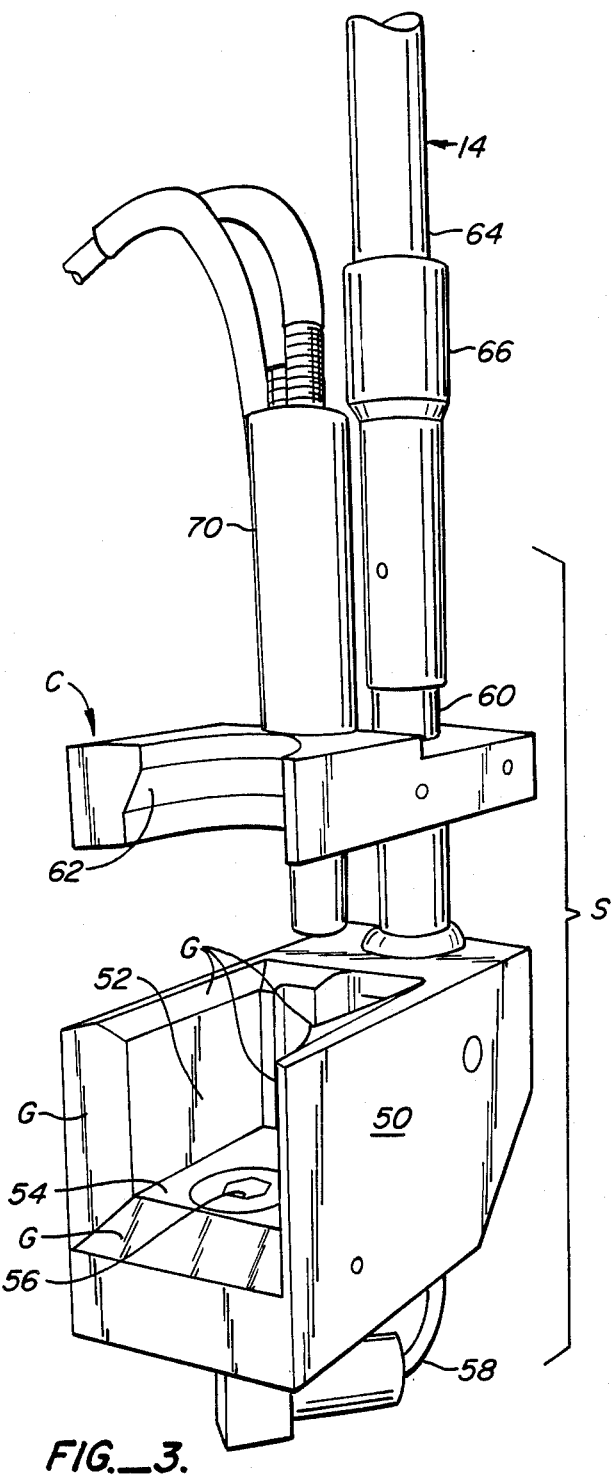
FIG._3.

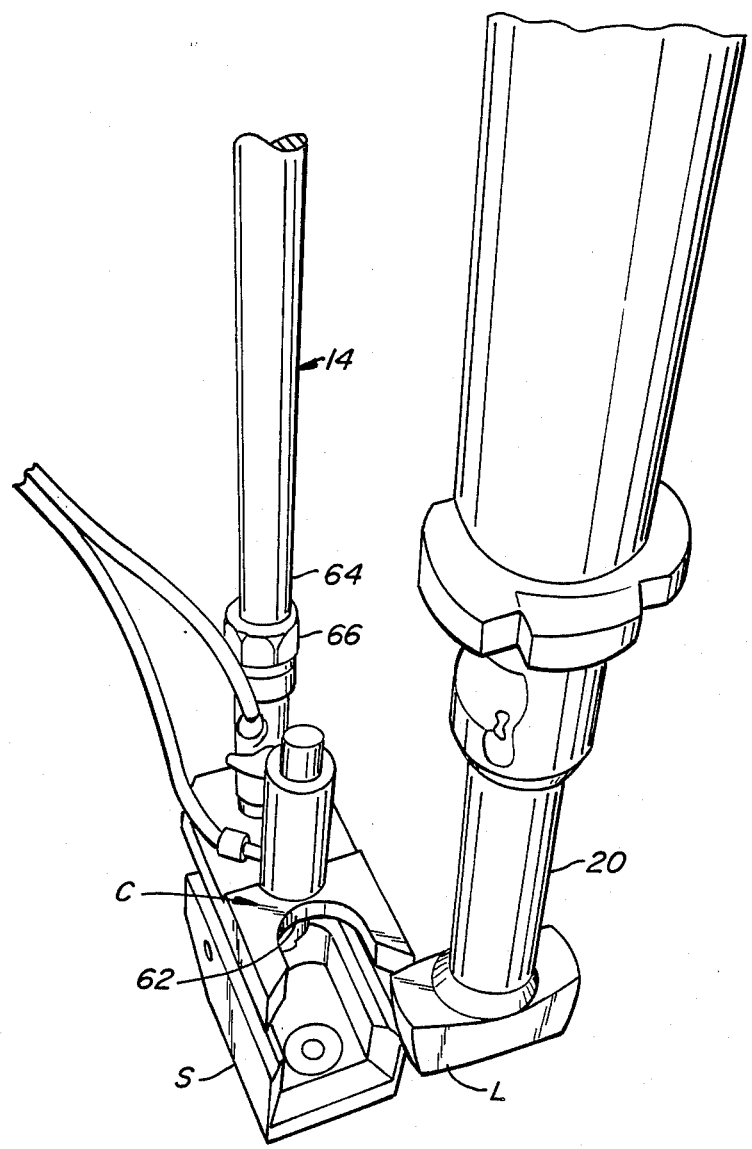
FIG._4.

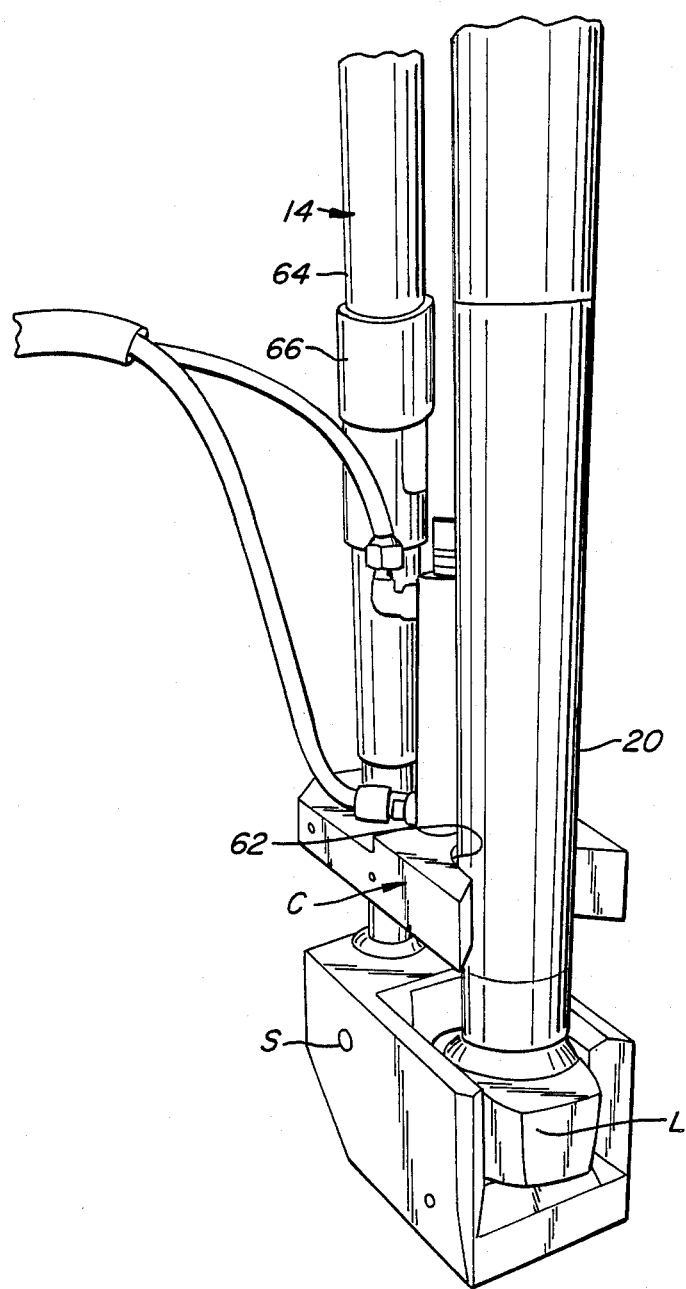
FIG._5.

APPARATUS FOR THE ULTRASONIC EXAMINATION OF SHROUD HOLD DOWN BOLTS

This invention relates to the ultrasound testing of steam separator hold down bolts in a boiling water nuclear reactor (BWR).

STATEMENT OF THE PROBLEM

BWRs are periodically refueled. As part of this refueling procedure, the reactor dome is removed, the steam dryer assembly lifted out of the reactor vessel and the cylindrical steam separator is then lifted out of the reactor vessel. The dome, dryer and separator are placed in a holding pool so that water shields any radio activity from working personnel. This invention relates to a problem that is unique to the steam separator and provides for inspection of the shroud hold down bolts when the steam separator is in the holding pool.

When the reactor is assembled and operating, the steam separator must be held in position to a shroud overlying the reactor core. This holding of the steam separator in position is accomplished by the shroud hold down bolts.

The shroud hold down bolts are relatively complex bolt members. These bolt members are elongate, extending from the top of the steam separator assembly to the bottom of the steam separator assembly a distance of about 13 to 17 feet. The bolts are manipulated and operated from the top, and fasten the steam separator to the shroud overlying the reactor core at the bottom. Because these bolts are well known in the prior art, they will be set forth herein only in sufficient detail so that the problems that they generate with respect to periodic inspections can be understood.

The shroud hold down bolts are typically spaced at equal radial intervals around the cylindrical steam separator. Each bolt includes a central tension member and an outer compression sleeve member with both members extending substantially the entire length of the bolts. Because of the relative proximity of the bottom of the bolts to the top of the radioactive reactor core, the bottom of the bolts are highly radioactive.

The lower portion of the inner tension member has a lug which is rectangular in plan on the bottom for engagement with a bracket on the shroud at the top of the core. This rectangular lug rotates from a radial alignment where release of the bolt from a mating shroud bracket can occur to a position normal to a radial alignment where attachment of the bolt at the rectangular lug to the shroud bracket can occur. When the rectangular lug is engaged with the bracket, the outer compression member bears down on the lower portion of the steam separator, places the inner member under tension from the shroud bracket and holds the steam separator to the rest of the reactor during operation.

All manipulations relating to the tightening or the loosening of the bolts occurs from the very top of the bolts. This enables engagement and disengagement of the bolts to be remotely manipulated, typically in a submerged disposition, so that radio activity is not a threat to operating personnel.

Tightening of the engaged bolts can be easily understood.

The bolts are tightened and loosened from the top of the steam dryer assembly. Assuming that the lug is engaged with the bracket, the outer compression sleeve of the bolt is forced downwardly over the inner tension member. The outer compression member bears downwardly on the lower portion of the steam separator. At the same time, the inner tension member pulls upwardly into the bracket on the shroud at the top of the reactor core. The result is that the steam separator is held to the top of the shroud overlying the core.

Loosening of the bolts is more complex. Adjacent the bottom of the bolts, attached to the outer compression member below the attachment at the bottom of the steam separator is a sleeve. This sleeve has a window. The purpose of the window is to maintain the lugs of the bolts in the open position when the bolts are fully loosened.

The lower end of the inner tension member is transpierced with a shaft normal to the sleeve. This shaft extends through the window in the sleeve. The purpose of the shaft is to co-act with a notch in the window of the sleeve to maintain the shroud bolt with its lug in the open position once it is fully loosened.

When the shroud bolt is fully loosened, the rectangular lug at the bottom of the tension member falls below the shroud bracket. When the rectangular lug falls below the shroud bracket, it is free to rotate. Rotation of the rectangular lug and the attached tension member occurs to a position where the lug is radially aligned with respect to the shroud bracket. With such radial alignment, release from the shroud bracket can occur.

Likewise, when the tension member and its rectangular lug rotate, the shaft in the window likewise rotates. This rotation of the shaft in the window continues until the rectangular lug is radially aligned and the transpiercing and protruding shaft engages the notch in the window of the sleeve. Once engagement to the notch in the window of the sleeve occurs, the rectangular lug at the bottom of the tension member is maintained in a position of radial alignment where release from the shroud bracket can occur.

Assuming that all shroud bolts are fully loosened and their respective lugs retained in the radially aligned position, lifting the steam separator from the shroud overlying the core can occur. Movement of the steam separator to the holding pool takes place.

Unfortunately, such shroud hold down bolts crack. The bolts crack on the inner tension member adjacent the lug, usually under the sleeve. They are subject to a metallurgical cracking phenomena known as inter granular stress crack corrosion. Simply stated, the oxygen in the water of the reactor combined with both the material and the tension on the bolts can cause cracking to occur. This cracking is intermittent and highly unpredictable.

Further, the cracking defect is latent in at least two respects. First, inter granular stress crack corrosion (IGSCC) is hard to locate by observation—for example an under water TV camera. Second, the most susceptible location for the IGSCC has been found to be a location underneath the locking sleeve at the bottom of the bolt.

Conventional inspection techniques are not desirable. Any inspection technique that involves removal and manipulation of the highly radioactive bolts is prohibitively expensive. Further, since the presence of the cracking is highly intermittent, routine inspection capability is desired for checking against this shroud bolt defect.

The reader will understand that the complete understanding of the latent defect is relatively complex. Consequently, insofar as understanding of the problem to be solved constitutes invention, invention is claimed.

SUMMARY OF THE PRIOR ART

Ultra sonic testing is known. Typically, piezoelectric transducers are directly placed by hand upon a member to be tested. A sonic signal is imparted to the member. The transducer listens for a returned and reflected signal. Once the signal is returned analysis of the tested member can be made.

Such ultra sound waves when transducing a rod such as the inner tension member have three types of waves traveling through the rod. These waves include longitudinal waves, refracted waves, and shear waves. It is by the analysis of these wave forms, that defects can be located. Since the analysis of such wave forms is well known in the prior art, further discussion will not be added here.

SUMMARY OF THE INVENTION

An apparatus for the remote examination of peripheral shroud hold down bolts on steam separators used in boiling water reactors (BWRs) is disclosed. The shroud hold down bolts surround the generally cylindrical steam separator at the outside circumference and are generally coextensive in length with the steam separator length, being in the order of 150 to 205 inches in length. During reactor outages, all bolts—between 24 and 48 in number—have rectangular holding lugs at the bottom of the hold down bolts radially aligned with respect to the steam separator to clear mating brackets on a shroud overlying the reactor core. When all bolts have their lugs radially aligned for release the steam separator with its attached bolts is moved to a holding pool and remains immersed in water to protect maintenance personnel from ambient radioactivity. The testing apparatus normally is used while the steam separator is in the holding pool with its respective lugs radially aligned. The testing apparatus includes a depending pole having attached at the bottom thereof an aluminum shoe. The shoe has a flat, upwardly exposed bottom and opens to one side at gathering surfaces to receive the lower ends of the shroud bolts. The upwardly exposed bottom of the shoe defines an aperture through which an upwardly exposed piezoelectric device is exposed for direct contact with the bottom of the bolt. An overlying clamp member is provided to clamp the lug onto the bottom of the shoe for test. The clamp member defines a receiving slot to receive the shaft of the bolt immediately overlying the rectangular lug. This clamp member is positioned at the slot on the shaft overlying the rectangular lug and thereafter moved down to and towards the lug by a pneumatic cylinder. The clamp member slides over the shaft at the slot into contact with the top of the lug. The clamp member clamps the lug end of the bolt securely onto the upwardly exposed piezoelectric device on the upwardly exposed bottom of the shoe. A piezoelectric ultrasonic test is then run from the bottom and radioactive portion of the bolt to and towards the top of the bolt. Testing for longitudinal sound waves, refracted sound waves and shear sound waves for inter granular stress corrosion cracking can occur despite the radioactive and remote under water location of the bolts.

OTHER OBJECTS AND ADVANTAGES

An object of this invention is to set forth a test protocol for a reactor steam separator shroud bolt without necessitating removal of the bolt.

An advantage of the disclosed protocol is that regular testing of the bolts can occur concurrently with reactor outages concurrent to refueling. Further, no removal or disassembly of the steam separator is required for the disclosed test.

Further, it has been found that the outer compression member, sleeved about the inner tension member, does not interfere with the desired testing. In short, a highly advantageous and economical ultrasonic test is disclosed.

BRIEF DESCRIPTION OF THE DRAWINGS

FIG. 1 is a perspective of a reactor illustrating the top of the reactor with the dome, and steam dryer removed and not shown with the reactor steam separator shown in a holding pool with repair personnel using the shroud bolt testing apparatus of this invention;

FIG. 2A and 2B are respective elevation and bottom plan views of the prior art shroud hold down bolt apart from the steam separator;

FIG. 3 is a perspective view of the testing shoe and clamp of this invention;

FIG. 4 is a perspective view of the testing shoe being manipulated over the lug at the bottom of the inner tension member of the shroud hold down bolt; and, FIG. 5 is a perspective of the testing shoe clamped to the bolt for test.

Referring to FIG. 1, a reactor R is illustrated adjacent a holding pool P. A steam separator S is shown removed from the reactor vessel R and placed within the holding pool. Man M manipulates a shoe S at the end of a long pole 14. Shoe S contains a flat bottom with an upwardly exposed piezoelectric device. As will hereinafter more fully appear, manipulation of pole 14 places the shoe S with the upwardly exposed piezoelectric device at the bottom and immersed end of shroud hold down bolt B. Consequently, an ultrasonic test may be conducted from the bottom immersed radioactive portion of the bolt to and toward the upper end of the bolt in the holding pool P.

It will be appreciated that the testing apparatus is flexible; testing of the bolts while the steam separator is in the reactor vessel may as well occur.

Referring to FIGS. 2A and 2B, the prior art shroud hold down bolt B can be understood. In pertinent part for the purposes of this application, shroud hold down bolt consists of two elongate members. First, there is an inner tension member 20. Inner tension member 20 is constructed of stainless steel and extends the full length of the bolt.

Tension member 20 includes a rectangular lug at the bottom thereof which is roughly rectangular in bottom plan view. (See FIG. 2B.) Lug L at the ends of its rectangular section extends beyond the side edges of the inner tension member 20. The side edges 22, 24 of this rectangular lug engage brackets on the shroud 30 overlying the reactor core.

The bolt also includes an outer compression tube or member 26 surrounding tension member 20. Compression member 26 compresses downwardly onto the lower portion of the steam separator at a collar 28.

The interaction between the lug L and the collar 28 is easy to understand. Specifically, and when the bolt is tightened lug L moves upwardly to and toward collar 28. Lug L, however, is attached underneath a bracket on the reactor shroud.

Collar 28 rides on the lower portion of the steam separator. When the bolt is tightened, the steam separator is pushed down onto the shroud bracket. Consequently, attachment of the steam separator to the shroud occurs.

As pertinent to the disclosure herein, collar 28 has a sleeve 40 directly fastened to the collar and extending below the collar to and towards lug L. Sleeve 40 is apertured with a window W. Window W includes a lower notch N.

Rod 20 is transpierced with a pin P. Pin P protrudes outwardly from the side of shaft 20 through the window W. It is the action of pin P in moving into and out of notch N which causes lug L to move to and from an unlocked position.

Simply stated, a mechanism M effects loosening and tightening of the bolt B utilizing a prior art thread driven apparatus. When mechanism M loosens lug L with respect to collar 28, pin P falls downwardly in window W. This downwardly falling disposition occurs until such time as lug L clears the lower portion of the bracket 30 attached to the shroud of the reactor R. Once lug L has cleared the bracket, rectangular lug L rotates until radial alignment to the steam separator occurs. This rotation of the rectangular lug L into radial alignment also aligns pin P directly over notch N. Further loosening of the bolt continues. This loosening continues until the pin P moves downwardly into and within notch N. Once this occurs, lug L is held in the unlatched position.

The importance of such a mechanism can be easily understood. Assuming there are 48 bolts securing a steam separator to a reactor shroud 30, all must be unlatched before any upward removal movement of the steam separator S can occur. If one or two bolts remain secured, the reader will understand the damage to the bolts, steam separator or reactor shroud could well occur in the lifting process.

It has been emphasized that sleeve 40 contributes to a latent defect in the rod 20. Specifically. and due to welding and other construction of the rod 20, intergranular stress corrosion cracking has been known to occur underneath sleeve 40. When such cracking occurs, sleeve 40 obscures from view the resultant cracks.

Moreover, the pin P co-acting with the window W and the notch N hold and maintain the lug L to the bolt B. Simply stated, even where the bolt B at tension member 20 is cracked through, the defect is latent.

It will be understood that lug L is highly radioactive. Referring to FIG. 1, the reader can see that this lug is immediately adjacent the core C of the reactor.

Having set forth the problem environment, the solution to the problem can now be set forth with respect to FIGS. 3, 4, and 5.

Referring to the perspective view of FIG. 3, shoe S is illustrated. The shoe includes a rectangular block shaped member 50 configured with a rectangular sectioned concavity 52. Just as lug L is rectangular in section (see FIGS. 2A and 2B), cavity 52 within shoe 50 is also rectangular in complementary section.

The cavity 52 includes a bottom surface 54. Configured centrally of the bottom surface 54 and upwardly exposed for contact at the bottom of the lug is a piezoelectric device 56. This piezoelectric device is placed within a defined aperture and is suitably connected by wires 58 to instrumentation (not shown).

It will be remembered that shoe S is remotely manipulated some 20 feet from the users. Consequently, the shoe is provided on all surfaces adjacent cavity 52 with gathering surfaces G. These gathering surfaces enable the device to conveniently find, slide onto, and fit lug L.

Once shoe S is in place over a lug L, a clamp member C at a defined grove 62 mate to tension member 20 immediately overlying rectangular lug L. Clamp member C moves downwardly onto and over shaft 20 at groove 20 until contact with the top of the rectangular lug L occurs. Such downward movement is actuated about shoe shaft 60 by a pneumatic cylinder 70. Such movement traps lug L within the cavity against the piezoelectric device 56. Thereafter, ultrasound testing of the shroud bolt can occur.

Referring to FIG. 4, a shoe S is shown adjacent a lug L with a pole 14 manipulating the shoe onto the end of the lug L. Attachment of the pole to the shoe S can be easily understood. The pole 14 includes a shaft 64. Shaft 64 on the pole 14 threads into an L shaped notch on tube 66 filling over pole 14 and attached to shoe S. Consequently, shoe S can be remotely manipulated onto and off of rectangular lug L for the test herein described.

Referring to FIG. 5, shoe S is shown clamping lug L onto the piezoeleotric device (hidden from view). Testing of the shroud bolt can occur.

What is claimed is:

1. In a nuclear reactor system having a hold down bolt attached to a steam separator within reactor water for the prevention of radioactive exposure to testing personnel, said bolt having an inner, lower tension member with a rectangular engaging lug, and an outer, coaxial compression bolt member, an apparatus for testing the tension member at the lug, comprising:
    a shoe;
    means for attachment of a pole to the top of said shoe to permit submersed manipulation of said shoe;
    a piezoelectric device mounted to the bottom of said shoe and exposed upwardly to and toward said tension member of said bolt for contacting said tension member at said lug for nondestructive piezoelectric testing of said tension member from said lug at the bottom of said bolt to and toward the top of said bolt;
    a clamp member for reciprocal movement towards and away from said shoe member;
    means mounting said clamp member for reciprocal movement towards and away from said shoe for releasably clamping said lug against said shoe at said piezoelectric device for ultrasonic testing of said inner tension member of said bolt with ultrasonic sound from said piezoelectric device.

2. The invention of claim 1 and wherein said shoe defines a concavity for receiving the bottom of said bolt.

3. The invention of claim 2 and wherein said shoe has an end wall and two side walls to define said concavity.

4. The invention of claim 1 and wherein said bolt has a shaft, and said clamp member defines an open shaft receiving aperture for sliding movement on the shaft of said bolt.

5. A process of testing hold down bolts depending from the sides of a steam separator within a nuclear reactor, said process comprising the steps of:
    maintaining said steam separator under water;

moving said bolts to unlatch said bolts from brackets on said shroud adjacent said steam separator;

providing a shoe having a piezoelectric device mounted to the bottom of said shoe and exposed upwardly;

providing a remotely actuated clamp attached to said shoe overlying said piezoelectric device;

providing a mount to said shoe for manipulating said shoe underwater in a depending relationship at the bottom end of a pole;

providing a pole and attaching said pole to said shoe;

manipulating said shoe to the bottom of said bolt;

clamping said shoe to said bolt; and testing said bolt with said piezoelectric device.

* * * * *